United States Patent [19]

Blythin et al.

[11] Patent Number: 5,118,683
[45] Date of Patent: Jun. 2, 1992

[54] ESTERS OF 4-HYDROXY-1,3-BENZENEDIMETHANOL AND COMPOSITIONS AND METHODS EMPLOYING SUCH COMPOUNDS

[75] Inventors: David J. Blythin, North Caldwell; Ho-Jane Shue, Pine Brook, both of N.J.

[73] Assignee: Schering Corporation, Kenilworth, N.J.

[21] Appl. No.: 537,384

[22] Filed: Jun. 13, 1990

[51] Int. Cl.⁵ ............................................. A61K 31/53
[52] U.S. Cl. .................................... 514/242; 514/247; 514/255; 514/269; 514/354; 514/355; 514/356; 514/361; 514/365; 514/374; 514/400; 514/406; 514/419; 514/448; 514/466; 514/471; 514/512; 514/546; 514/548; 514/533; 544/182; 544/224; 544/335; 544/389; 546/263; 548/128; 548/201; 548/236; 548/343; 548/377; 549/71; 549/74; 549/484; 549/486; 549/468; 558/273; 560/109; 560/170; 560/252
[58] Field of Search ............ 560/109, 170, 252; 574/533, 512, 448, 471, 466, 546, 548, 242, 247, 255, 269, 354, 355, 356, 361, 365, 374, 400, 406, 419; 558/273; 549/74, 484, 486, 468, 71; 546/263; 548/128, 201, 236, 343, 377, 492; 544/182, 224, 335, 389

[56] References Cited

U.S. PATENT DOCUMENTS 3,644,353  2/1972  Lunts et al. ............... 260/247.5 R
3,904,671  9/1975  Minatoya et al. ........... 260/473 R

FOREIGN PATENT DOCUMENTS 1298771  12/1972  United Kingdom .

Primary Examiner—Bruce Gray
Attorney, Agent, or Firm—Matthew Boxer; Henry C. Jeanette

[57] ABSTRACT

Compounds of the formula I

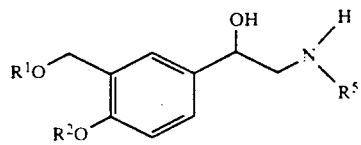

wherein
$R^5$ represents $C_1$ to $C_6$-alkyl or the group —$(CH_2)_n$—Z—$(CH_2)_m$—Ar;
Z represents O, S or —$CH_2$—;
n represents an integer of 1 to 8;
m represents zero or an integer of 1 to 8;
one of $R^1$ and $R^2$ represents the group

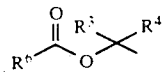

and the other represents hydrogen or $R^7CO$—;
$R^7$ is $C_1$ to $C_{10}$ alkyl, $C_3$ to $C_8$ cycloalkyl, aryl, heteroaryl, —$N(R^9R^{10})$, or $R^{11}O$—; $R^3$, $R^4$, $R^9$, and $R^{10}$ are each independently selected from hydrogen, $C_1$ to $C_6$ alkyl and $Ar^1$; $R^6$ and $R^{11}$ are each independently $C_1$-$C_8$ alkyl; Ar and $Ar^1$ are each independently selected from the group consisting of phenyl or phenyl substituted by one or two substituents selected from the group consisting of $R^{12}$, $R^{13}O$—; $R^{14}S(O)_x$—, $R^{15}CO$—, $(R^{16}R^{17})NCO$—, F, Cl, Br, I, $NO_2$, $CF_3$, CN, or phenyl; $R^{12}$, $R^{13}$, $R^{14}$, $R^{15}$, $R^{16}$, and $R^{17}$ each independently represents an alkyl group having 1 to 6 carbon atoms; x is 0, 1, or 2;
or a pharmaceutically acceptable acid addition salt thereof are described.

These compounds provide $\beta_2$-agonist activity, and possess favorable properties for the treatment of asthma and all types of chronic obstructionary pulmonary diseases.

18 Claims, No Drawings

ESTERS OF 4-HYDROXY-1,3-BENZENEDIMETHANOL AND COMPOSITIONS AND METHODS EMPLOYING SUCH COMPOUNDS

BACKGROUND OF THE INVENTION

This invention relates to certain esters and/or ethers of known $\beta_2$-agonists, which esters and/or ethers possess favorable properties for the treatment of asthma and all types of chronic obstructionary pulmonary diseases (COPD).

$\beta_2$-agonists are well known in the art, e.g. albuterol which is described in U.S. Pat. No. 3,644,353. Certain esters of albuterol or compounds closely related to albuterol have also been described, e.g. in U.S. Pat. No. Re. 30,241, British Patent No. 1,298,771, U.S. Pat. No. 3,904,671. However, none of these publications describe or suggest the ester and/or ethers of this invention.

SUMMARY OF THE INVENTION

The compounds of this invention are of the formula I

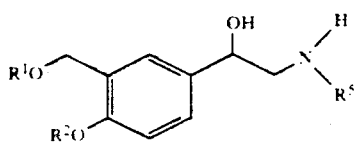

wherein $R^5$ represents $C_1$ to $C_6$—alkyl or the group —$(CH_2)_n$—Z—$(CH_2)_m$—Ar;

Z represents O, S or —$CH_2$—;

n represents an integer of 1 to 8;

m represents zero or an integer of 1 to 8;

one of $R^1$ and $R^2$ represents the group

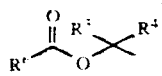

and the other represents hydrogen or $R^7CO$—;

$R^7$ is $C_1$ to $C_{10}$ alkyl, $C_3$ to $C_8$ cycloalkyl, aryl, heteroaryl, —$N(R^9R^{10})$, or $R^{11}O$—; $R^3$, $R^4$, $R^9$, and $R^{10}$ are each independently selected from hydrogen, $C_1$ to $C_6$ alkyl and $Ar^1$; $R^6$ and $R^{11}$ are each independently $C_1$-$C_8$ alkyl; Ar and $Ar^1$ are each independently selected from the group consisting of phenyl or phenyl substituted by one or two substituents selected from the group consisting of $R^{12}$, $R^{13}O$—, $R^{14}S(O)_x$—, $R^{15}CO$—, $(R^{16}R^{17})NCO$—, F, Cl, Br, I, $NO_2$, $CF_3$, CN, or phenyl; $R^{12}$, $R^{13}$, $R^{14}$, $R^{15}$, $R^{16}$, and $R^{17}$ each independently represents an alkyl group having 1 to 6 carbon atoms; x is 0, 1, or 2;

and pharmaceutically acceptable acid addition salts thereof.

The compounds of formula I are preferably salts.

In the compounds of the invention, $R^1$ preferably represents

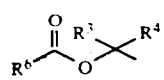

and $R^2$ preferably represents

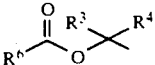

wherein $R^3$, $R^4$, $R^6$ and $R^7$ are as defined above. Alternatively, $R^1$ preferably represents $R^7$—CO— and $R^2$ preferably represents

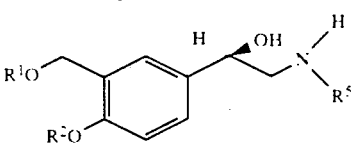

wherein $R^3$, $R^4$, $R^6$ and $R^7$ are as defined above.

$R^5$ preferably represents tertiary-$C_4H_9$, iso-$C_3H_7$ or —$(CH_2)_n$—O—$(CH_2)_m$—phenyl wherein n and m independently are integers of 2 to 6.

$R^3$ and $R^4$ both preferably represents H. $R^6$ preferably represents $C_3$ to $C_6$ alkyl. $R^7$ preferably represents $C_1$ to $C_6$ alkyl, phenyl, substituted phenyl, or unsubstituted heteroaryl, more preferably, $C_1$ to $C_6$ alkyl, phenyl or substituted phenyl.

The compounds of the invention preferably have the structural configuration

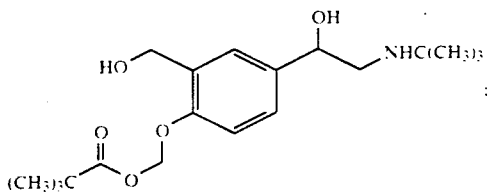

wherein $R^1$, $R^2$, and $R^5$ are as described above.

Representative compounds of the invention have the structural formulas:

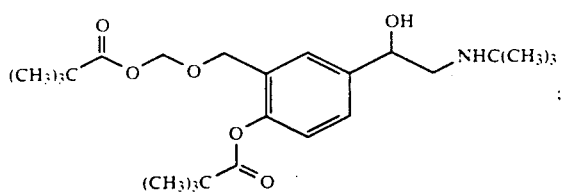

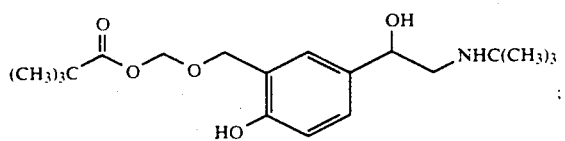

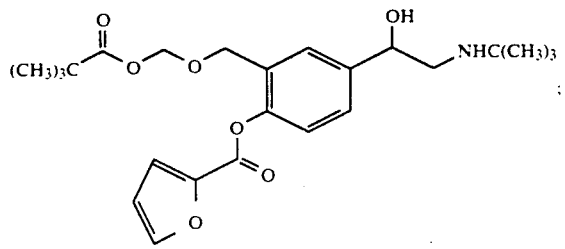

-continued
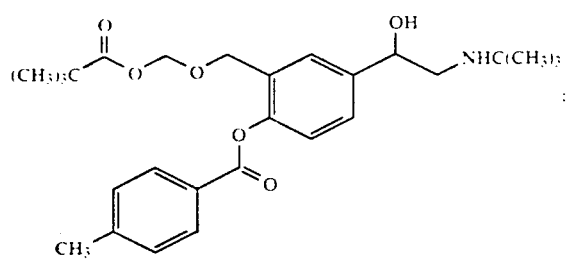
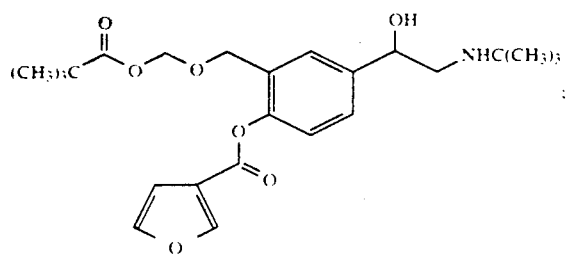
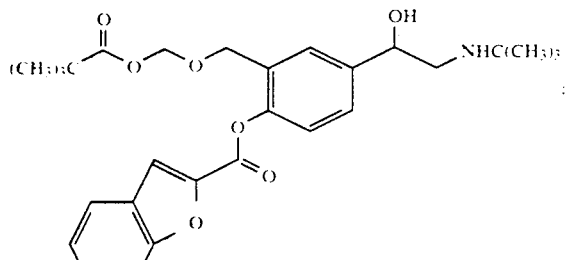
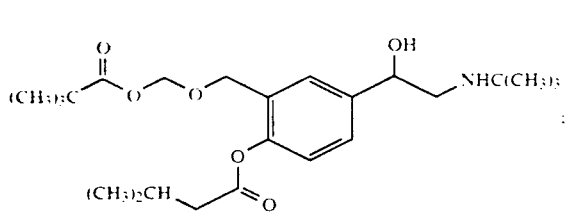
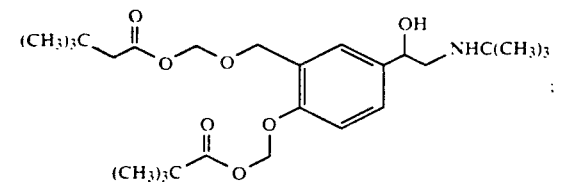
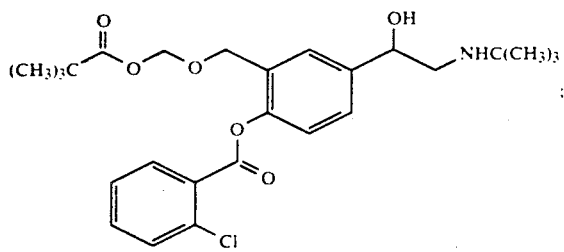
-continued
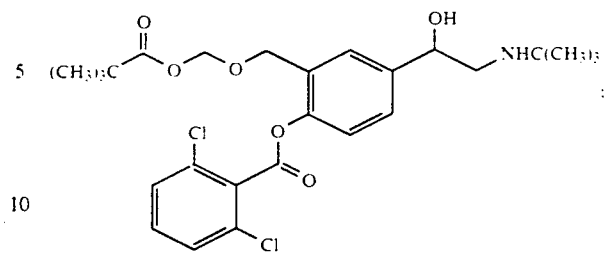
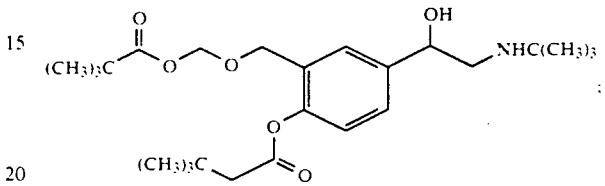
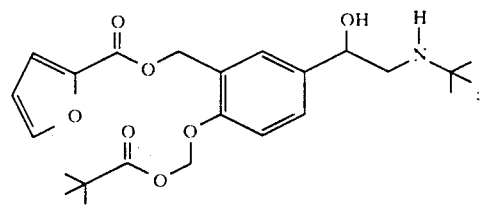
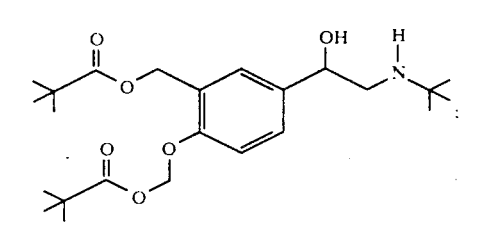
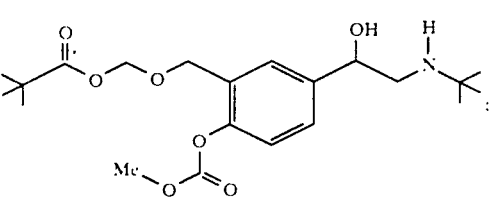
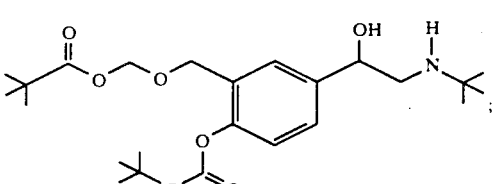
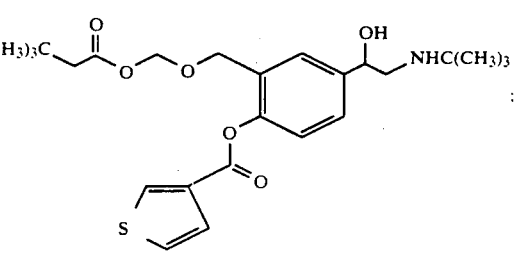

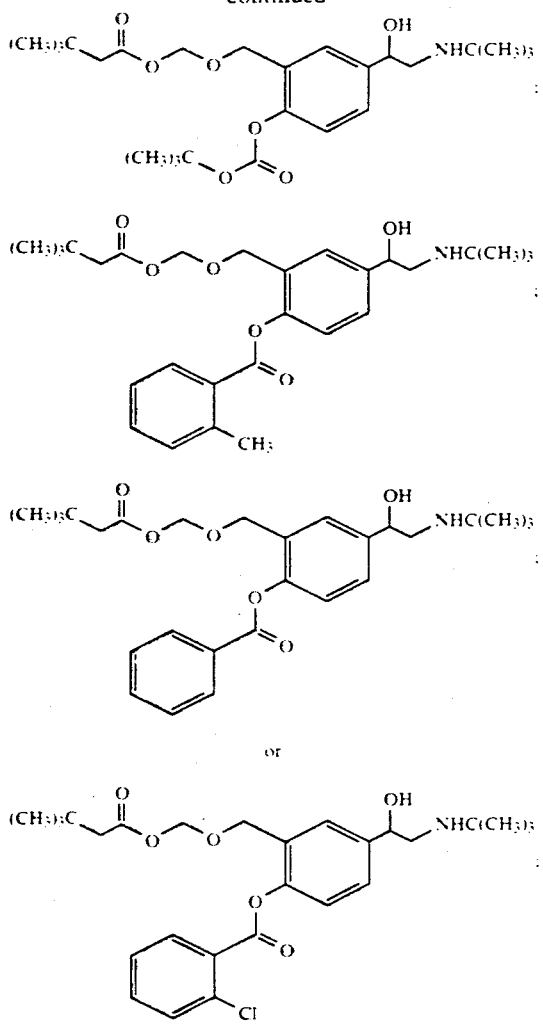

-continued

A particularly preferred compound is

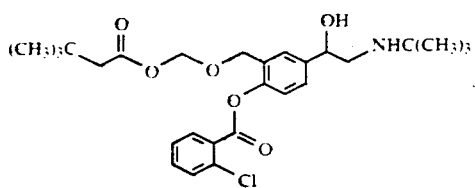

The invention also relates to pharmaceutical compositions comprising a compound of formula I above in salt form in combination with a pharmaceutically acceptable carrier and methods of treating asthma, asthmatic bronchitis and other forms of obstructive pulmonary disease by administering an effective amount of a compound of formula I above for such purpose.

DETAILED DESCRIPTION OF THE INVENTION

The following terms used in the specification and claims have the meanings indicated below, unless otherwise indicated:

alkyl (including the alkyl portions of alkoxy, alkylthio, etc.)—represents a straight or branched, saturated hydrocarbon chain having the number of carbon atoms designated. For example, $C_1$ to $C_6$ alkyl refers to an alkyl, as described just above, having 1 to 6 carbon atoms.

aryl—represents phenyl, 1-naphthyl, 2-naphthyl, phenanthrenyl, anthracenyl and indanyl, wherein the aryl group may be substituted by 1 to 3 substituents selected from the same group of substituents which may be attached to phenyl as hereinabove described and the aryl group may be attached via any ring carbon atom not occupied by another substituent;

heteroaryl—represents a cyclic group having at least one O, S and/or N interrupting a carbocyclic ring structure and having a sufficient number of delocalized pi electrons to provide aromatic character, with the aromatic heterocyclic group having from 2 to 14, preferably from 2 to 6 carbon atoms, e.g., 2-, 3- or 4-pyridyl, 2- or 3-furyl, 2- or 3-thienyl, 2-, 4- or 5-thiazolyl, 2-, 4- or 5-imidazolyl, 2-, 4- or 5-pyrimidinyl, 2-pyrazinyl, 3- or 4-pyridazinyl, 3-, 5- or 6-[1,2,4-triazinyl], 3-or 5-[1,2,4-thiadiazolyl], 2-, 3-, 4-, 5-, 6- or 7-benzofuranyl, 2-, 3-, 4-, 5-, 6- or 7-indolyl, 3-, 4- or 5-pyrazolyl, 2-, 4- or 5-oxazolyl, etc., wherein the heteroaryl group may be substituted by 1 to 3 substituents selected from the same group of substituents which may be attached to phenyl as hereinabove described and the heteroaryl group may be attached via any ring carbon atom not occupied by another substituent. Preferred heteroaryl groups are 2-, 3- or 4-pyridyl, 2-or 3-furyl, 2- or 3-thienyl, 2-, 4- or 5-imidazolyl and 7-indolyl.

Certain compounds of this invention may exist in isomeric forms. The invention contemplates all such isomers both in pure form and in admixture, including racemic mixtures.

Certain compounds of the invention of formula I can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of the invention.

The compounds of the invention form pharmaceutically acceptable salts with organic and inorganic acids. Examples of suitable acids for such salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form preferably of a suitable precursor such as a compound of formula VI(a) or a compound of formula VI(b) as described below with a sufficient amount of the desired acid to produce a salt in the conventional manner, and carrying these intermediates through to the final products according to the procedures described below. The free base forms differ from their respective salt forms somewhat in certain physical properties, such as solubility in polar solvents, but the salts are otherwise equivalent to their respective free base forms for purposes of this invention.

The compounds of this invention may be prepared according to methods well known in the art. In the reaction schemes below, $R^1$, $R^2$, $R^3$, $R^4$, $R^5$, $R^6$, and $R^7$ are as described above unless otherwise noted.

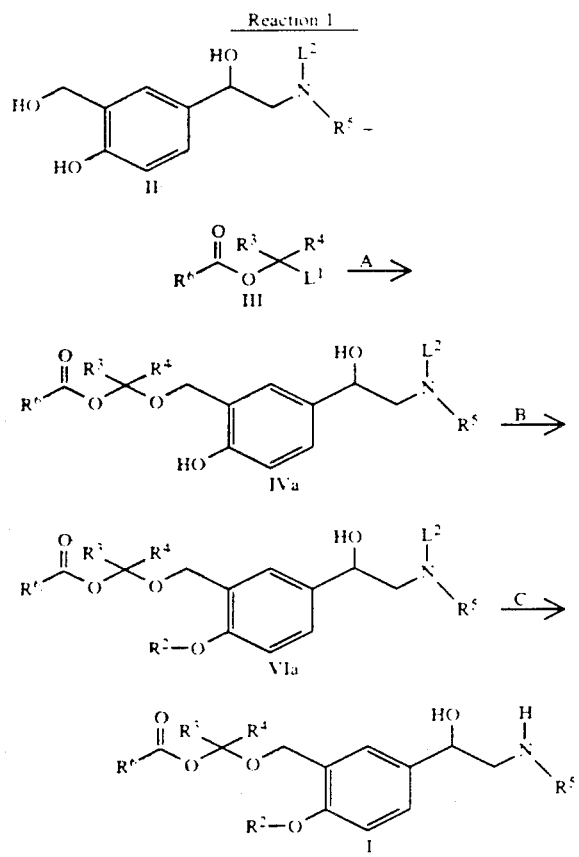

Reaction 1

In the above formulae, $L^1$ is a leaving group, e.g. halogen such as bromine, chlorine, or iodine, with iodine being preferred because $L^1$ is iodine in the immediately preceding step of the chemical synthesis; and $L^2$ represents a protecting group such as benzyl, alkyl- or alkoxy- substituted benzyl, or benzhydryl.

Step A is preferably carried out in a neutral solvent, e.g., dimethyl formamide (DMF), methyl ethyl ketone, or more preferably, acetone, in the presence of a base, e.g. sodium carbonate, cesium carbonate, or more preferably, $K_2CO_3$, by rapidly adding a solution of compound III to compound II at room temperature under an inert atmosphere such as argon or nitrogen. The reaction is conducted for a period of about 1 to about 100 hours, and the resulting product of formula IVa may be isolated by conventional means.

In the above reaction, the compound of formula III may be prepared in situ. For example, the corresponding compound of formula III, that is, a compound of formula

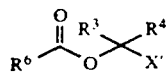

wherein $R^3$, $R^4$, and $R^6$ are as described above, and X' is chloro may be reacted with a salt such as sodium iodide, or more preferably, potassium iodide, in the presence of a solvent such as an aliphatic ketone, preferably acetone, to obtain a compound of formula III in which $L^1=I$, which is reacted in situ with a compound of formula II as described above. This in situ reaction is carried out at about room temperature in an inert atmosphere such as argon or nitrogen.

If a compound of formula I wherein $R^2$ is hydrogen is desired, then compound IVa obtained by reaction step A or preferably an acid addition salt thereof may be subjected to removal of the protecting group $L^2$. For example, if $L^2$ is benzyl it may be removed by hydrogenolysis. The hydrogenolysis may be carried out in a polar organic solvent such as acetic acid or an alcohol, like ethanol, butanol, or more preferably a mixture of methylene chloride and isopropanol. The reaction is carried out in the presence of a hydrogenation catalyst such as $PtO_2$, Pt on carbon, or Pd on carbon, more preferably 10% Pd-C. The hydrogenation is done in about 1 to about 3 atmospheres of $H_2$, preferably about 1 atmosphere of $H_2$ for a period of about 0.25 to about 30 hr., preferably about 0.25-3 hours. Isolation of the thus obtained compound of formula I can be by conventional means such as filtration followed by evaporation of the solvent, and purification of the residue by column chromatography.

In step B of the above process a compound of formula IVa is reacted with an acid chloride ($R^7COCl$) or acid anhydride ($R^7$—CO)$_2$O to yield a compound wherein $R^2$ is $R^7$—CO. The reaction is preferably carried out in a neutral solvent, e.g. $CHCl_3$, or preferably $CH_2Cl_2$, in the presence of a base such as pyridine, diisopropyl ethylamine, or more preferably triethylamine at temperatures between $-78°$ and $0°$ C. under an inert atmosphere such as argon or nitrogen. Preparation of the acid addition salt and removal of the protecting group $L^2$, e.g. as described above, result in an acid addition salt of a compound of formula I. (Step C).

If in step A above, the reaction is carried out by dropwise addition of compound II in a neutral solvent, or more preferably acetone, to a solution of III in acetone, a compound of formula IVb below is obtained. By following the further reactions outlined above, compounds of formula I wherein $R^1$ is hydrogen or $R^7$—CO, i.e. compounds of formula (Ib) are obtained through the intermediate VI b set forth just below.

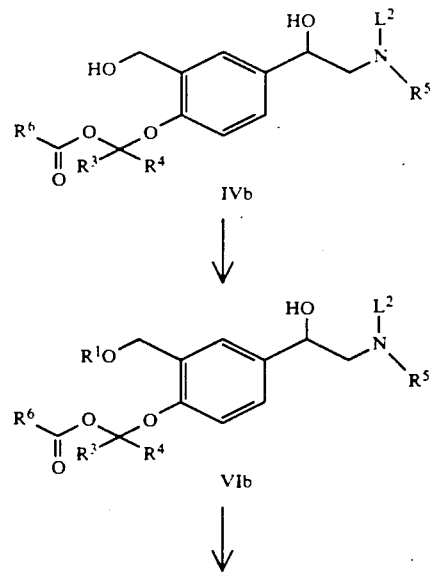

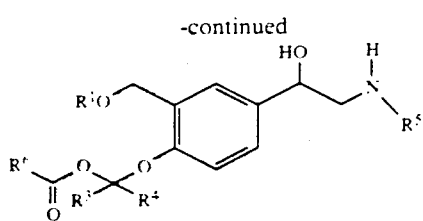

Ib

The following reaction steps also lead to compounds of formula I wherein $R^1$ is $R^-$—CO:

Reaction 2.

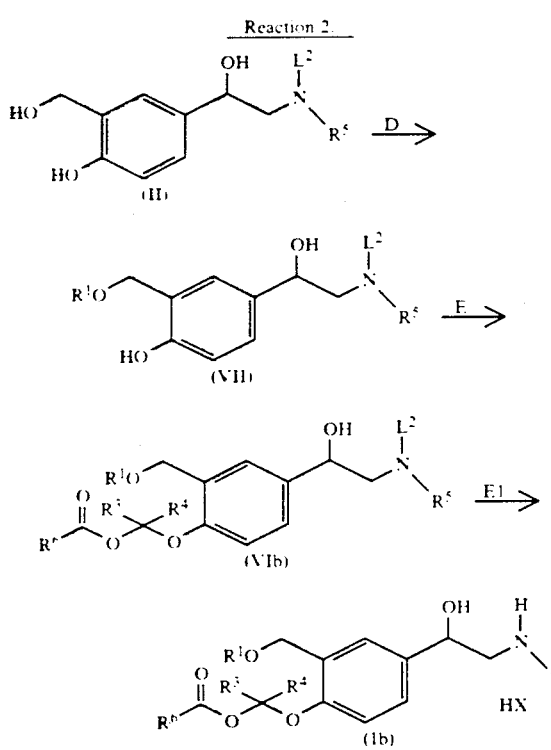

In step D the triol II is reacted with an acid chloride or acid anhydride as described under step B in Reaction 1 above resulting in a compound of formula VII which may be isolated and purified by flash chromatography. Reaction of a compound of formula VII with a compound of formula III (see step A Reaction 1) in a neutral solvent, e.g. acetone, in the presence of a base, e.g. $K_2CO_3$, results in a compound of formula VIb which is then transformed into an acid addition salt by treatment with a slight excess of acid, e.g. HCl. The salt is dissolved in isopropyl alcohol (using $CH_2Cl_2$ as a cosolvent if necessary) and treated with hydrogen over 10% Pd-C. The so obtained compound of formula Ib is purified by flash chromatography, short path column chromatography or reversed phase HPLC (high performance liquid chromatography).

The starting compounds used in the reactions described above are either known compounds or may be obtained by reaction steps well known in the art for preparing similar compounds, e.g. by following the reactions indicated below:

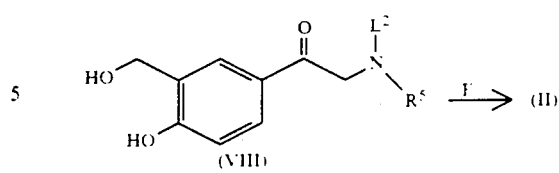

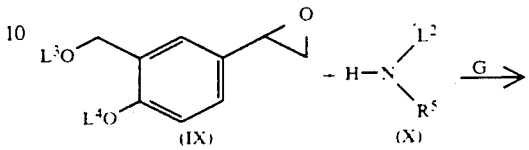

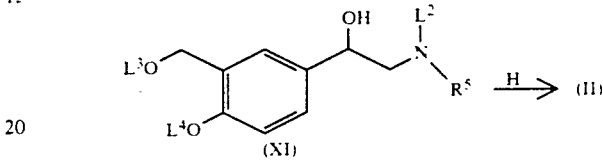

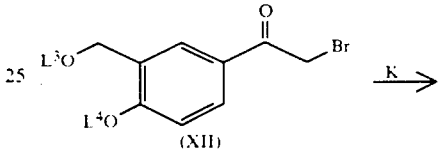

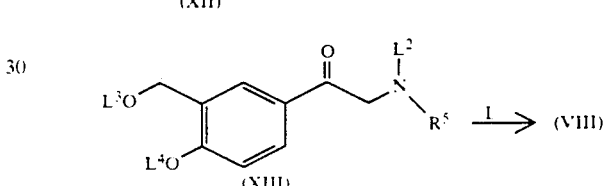

In reaction F, reduction of the carbonyl group in compound VIII with $NaBH_4$ leads to a starting compound of formula II. The reduction is carried out in a solvent such as an alcohol, or more preferably, isopropanol at a temperature of from about $-10°$ C. to about $20°$ C. A compound of formula II may also be obtained by reaction of the amine of formula X with the epoxide of formula IX in a neutral solvent such as tetrahydrofuran (THF), DMF, or more preferably, $CH_2Cl_2$ at a temperature of from about $-10°$ C. to about $35°$ C. The resulting compound XI is then hydrolyzed to eliminate the protecting groups $L^3$ and $L^4$. The hydrolysis is by conventional means. For example, a compound of formula XI may be reacted with an acid such as aqueous HCl, or more preferably aqueous $H_2SO_4$. The temperature is from about $10°$ C. to about $40°$ C. Alternatively, the hydrolysis may be conducted with a base such as an inorganic hydroxide, preferably NaOH or KOH. The temperature is from about $10°$ C. to about $50°$ C. Compounds of formula VIII may be prepared by reacting a compound XII with an amine of formula X followed by removal of the protecting groups $L^3$ and $L^4$ by hydrolyses. The reaction with the amine is conducted in a neutral solvent such as THF, DMF, or preferably $CH_2Cl_2$ at a temperature from about $0°$ C. to about $30°$ C. These hydrolyses are conducted similarly to hydrolyses described above.

$R^5$ is as defined for formula II and $L^2$, $L^3$ and $L^4$ represent standard protecting groups. For example, $L^2$ may be benzyl or substituted benzyl, whereas $L^3$ and $L^4$ may be ester groups, such as lower acyl (e.g. acetyl), or $L^3$ and $L^4$ may be joined together to form a ring in which a —CH₂—, —CHCH₃—, or —CH(phenyl)— bridges the two oxygen atoms.

Compounds of formula IX are well known in the art, e.g. from British Patent No. 2 140 800 A and German Patent No. 2 310 141.

Compounds of formulae VIII, X, XI, XII and XIII are also known or can be prepared in accordance with known methods.

The compounds of the invention provide bronchodilating activity with enhanced duration of activity compared to the known unprotected diols. Such enhanced duration of activity varies with the R² and R³ groups employed.

The bronchodilator activity provided by the compounds of the invention may be demonstrated by the following test protocol.

INHIBITION OF HISTAMINE INDUCED BRONCHOSPASM

Procedure

Male Charles River Hartley strain guinea pigs are fasted overnight but allowed H₂O ad lib. At −20 minutes, the animals are anesthetized with I.P. dialurethane. About 4 minutes later, the animals are shaved in the neck area and placed on their backs on a platform, inclined head up at 45° from horizontal. An incision is made through the skin and muscle/fascia teased apart to expose the trachea. Forceps are placed behind the trachea to hold it rigid while a 25 g ⅝″ needle attached to a 1 cc syringe is inserted between cartilage rings pointing caudally into the lumen of the trachea and 0.2 mL of control vehicle (saline) or test compound (3 μg in 0.2 mL) is injected slowly intratracheally at −15 minutes.

The needle and forceps are then removed and the animal is transferred to a platform inclined at about 30° from horizontal (still on its back) and surgically prepared by installing an intratracheal tube. The animal is respirated during surgery. The animals are then transferred to a different respirator and monitored for insufflation pressure using a side-arm pressure transducer. Pump volume is 4.0 mL and the rate is 55 strokes/min. The animals are challenged at 0 minutes with an I.V. 10 μg/kg histamine (HA) bolus. A second I.V. HA challenge is given at +30 minutes (i.e. 45 minutes post I.T. Rx).

Separate studies were conducted to determine whether bronchodilator activity lasted 3 hours. In these studies, the animals are first anesthetized with the short acting ingredient Brevital. Under anesthesia, the trachea is exposed and the compound is given (15 μg in 0.2 mL), as described above. The animal recovers from the anesthesia within 30 min and is allowed free movement for the next 2 hours. At that time, the animals are anesthetized with dialurethane and surgically prepared for the measure of insufflation pressure and I.V. challenge with histamine (3 hours after Rx) as described above.

The results obtained in the above procedures are shown in Table 1 and expressed as a percent inhibition of the bronchospasm (increased insufflation pressure) due to histamine.

The first dose, 3 μg (second column from left in table below) was used to test for onset of activity at 15 minutes, whereas the second dose, 15 to 25 μg, (fourth column from left in table below) was used to test for duration of activity at 3 hours.

| TABLE 1 | | | | |
|---|---|---|---|---|
| ACTIVITY IN GUINEA PIG BRONCHOSPASM ASSAY | | | | |
| STRUCTURE | Dose (μg) | % inhibn | Dose (μg) | % inhibn |
| [structure 1] | 3 | 76 | 25 | 37 |
| [structure 2] | 3 | 77 | 15 | 27 |
| [structure 3] | 3 | 82 | 15 | 21 |

TABLE 1-continued

ACTIVITY IN GUINEA PIG BRONCHOSPASM ASSAY

| STRUCTURE | Dose (μg) | % inhibn | Dose (μg) | % inhibn |
|---|---|---|---|---|
| (structure) | 3 | 75 | 15 | 0 |
| (structure) | 3 | 58 | 15 | 36 |
| (structure) | 3 | 63 | 15 | 32 |
| (structure) | 3 | 79 | 15 | 18 |
| (structure) | 3 | 79 | 15 | 24 |
| (structure) | 3 | 74 | 15 | 21 |
| (structure) | 3 | 94 | 15 | 23 |

TABLE 1-continued

ACTIVITY IN GUINEA PIG BRONCHOSPASM ASSAY

| STRUCTURE | Dose (μg) | % inhibn | Dose (μg) | % inhibn |
|---|---|---|---|---|
| [structure] | 3 | 57 | | |
| [structure] | 3 | 64 | 15 | 28 |
| [structure] | 3 | 53 | 15 | 37 |
| [structure] | 3 | 0 | 15 | 21 |
| [structure] | 3 | 74 | 15 | 64 |
| [structure] | 3 | 82 | 15 | 33 |

TABLE 1-continued

ACTIVITY IN GUINEA PIG BRONCHOSPASM ASSAY

| STRUCTURE | Dose (µg) | % inhibn | Dose (µg) | % inhibn |
|---|---|---|---|---|
| 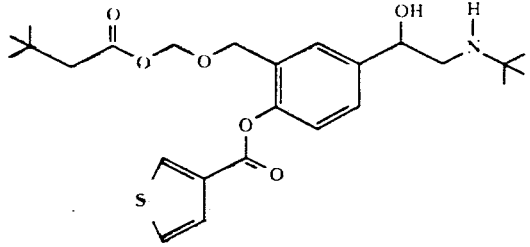 | 3 | 46 | | |
| 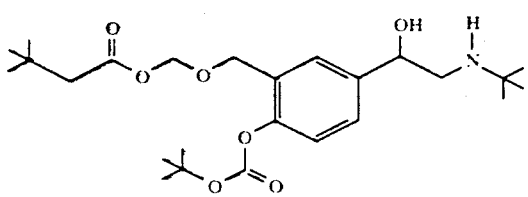 | 3 | 4 | | |
| 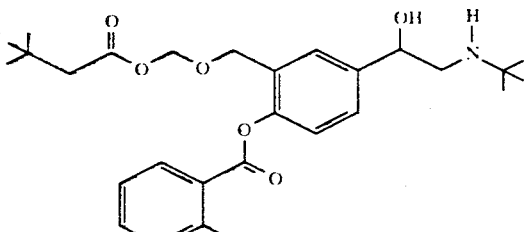 | 3 | 58 | 15 | 63 |
| 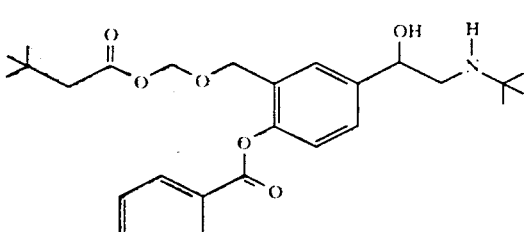 | 3 | 36 | | |
| 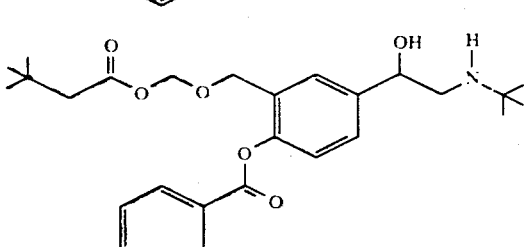 | 3 | 0 | | |

The active compounds can be administered orally, but are preferably delivered via aerosol, e.g., via oral or nasal inhalation.

The compounds can be administered in conventional oral dosage forms such as capsules or tablets prepared with conventional pharmaceutically acceptable excipients and additives, using conventional techniques. Inhalation administration can be in the form of a nasal or oral spray. Insufflation is also contemplated.

For preparing pharmaceutical compositions from the compounds described by this invention, inert, pharmaceutically acceptable carriers can be either solid or liquid. Solid form preparations include powders, tablets or capsules. The powders and tablets may comprise from about 5 to about 70 percent active ingredient.

Suitable solid carriers are known in the art, e.g., magnesium carbonate, magnesium stearate, talc, sugar, lactose.

Aerosol preparations suitable for inhalation may include solutions and solids in powder form, which may be in combination with a pharmaceutically acceptable carrier, such as an inert compressed gas. Normally, the formulation will be delivered from a dispensing or inhaling device, which would provide the preferred metered dose of the compound of the invention.

The oral dosage range is about 2 to about 20 mg daily per adult patient. This amount may be given in divided doses. For example two 10 mg capsules may be given to an adult patient for one day.

Preferably, the pharmaceutical preparation is in aerosol form. In such form, the preparation is delivered as unit doses containing appropriate quantities of the active component, e.g., an effective amount to achieve the desired purpose. When used in this way for the treatment of bronchoconstriction, the compounds of the invention can be administered in an amount ranging from about 50 μg to about 1000 μg per puff, preferably about 100 μg to about 500 μg per puff. A typical recommended dosage regimen is oral administration of from about 100 to about 2000 μg/day, preferably from about 200 to about 1000 μg/day, in two to four doses to achieve relief of the symptoms of bronchoconstriction.

Determination of the proper dosage of a compound of the invention for a particular situation is within the skill of the art. Generally, treatment is initiated with smaller dosages that are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of formula I and the pharmaceutically acceptable salts thereof will be regulated according to the judgement of the attending clinician considering such factors as age, condition and size of the patient as well as severity of the symptom being treated.

The invention disclosed herein is exemplified by the following preparative examples, which should not be construed to limit the scope of the disclosure. Alternative mechanistic pathways and analogous structures within the scope of the invention will be apparent to those skilled in the art.

EXAMPLE 1

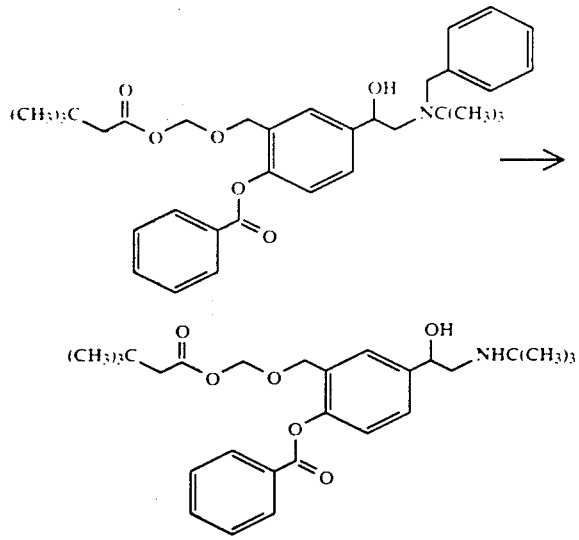

The starting material, prepared in essentially the same way as described in Preparative Example 3 below, (0.616 g), was dissolved in CH$_2$Cl$_2$ (5 mL) and isopropanol (IPA) (5 mL) in a hydrogenation flask containing 10% Pd-C (61.6 mg) flooded with N$_2$ gas. Methanesulfonic acid (78.3 μL) was added dropwise to the stirred solution. The suspension was stirred in a hydrogen atmosphere. The reaction was followed by (Thin Layer Chromatography) TLC until complete (about 2 hrs.).

The catalyst was removed by filtration and the solvents were evaporated under vacuum to yield an amber oil which was purified by column chromatography on silica gel eluting with CH$_2$Cl$_2$/10% methanol. The product, located by TLC, was obtained by evaporation of the relevant fractions and was dried under high vacuum overnight to yield 0.387 g of a hygroscopic white solid, which was shown to be a hydrated HCl salt of the desired material.

Analysis: C$_{27}$H$_{37}$NO$_6$·HCl·0.75 H$_2$O. Found: C, 61.87; H, 6.55; N, 2.73. Theory: C, 62.18; H, 7.63; N, 2.69.

FAB-MS: m/e 472 (M+1).

EXAMPLE 2

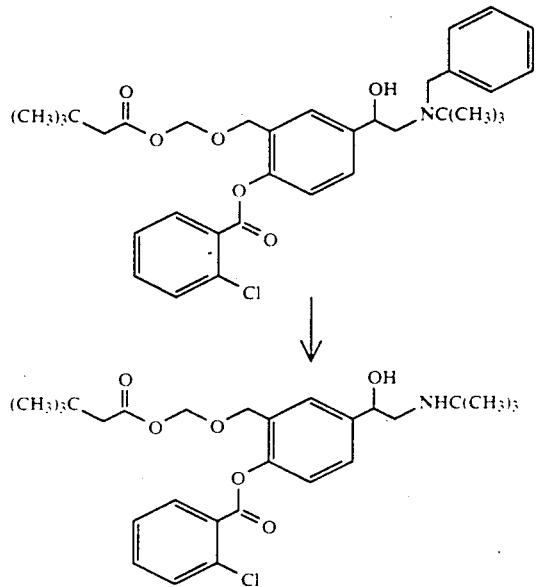

The product from Preparative Example 3, (2.39 g) was dissolved/suspended in IPA (238 mL). A slight excess of 20% HCl in methanol (0.88 mL) was added, the mixture was stirred for 10 min. and it was then evaporated to a white solid. This solid was redissolved in a mixture of methanol (23.8 mL) and ethanol (214.2 mL). To this solution was added 10% Pd-C (1.195 g) while the flask was flushed with N$_2$. The mixture was stirred and hydrogenolyzed under 1 atmosphere of H$_2$. The progress of the reaction was followed at about 15 minute intervals by reverse-phase high performance liquid chromatography (RP-HPLC). The reaction was terminated when dechlorination of the aromatic halogen began to be seen (around 8% conversion to dechlorinated product; no starting material left).

The catalyst was filtered off, and the reaction mixture was evaporated to dryness under vacuum. The crude product was dissolved in methanol:water (50:50; minimum volume) and purified by preparative RP-HPLC using a C$_4$-coated 300 A pore-size column with methanol (50%):water (50%), adjusted to pH 2.8-3.0 with HCl. The desired fractions were located by both TLC and RP-HPLC using a Whatman Partisil 5, ODS-3 (octadecyl silane) analytical column, eluting with methanol (80 parts) water (20 parts); 85% H$_3$PO$_4$ (1 part); sodium dodecyl sulfate (0.0025M). Detection was by UV absorption at 230 nm. The combined fractions containing product were evaporated under reduced pressure, at or below room temperature, to remove methanol, then the product was extracted with CH₂Cl₂ (3 × 1 L). The resulting solution was dried, filtered, and evaporated to yield the product as a white foam.

EXAMPLE 3

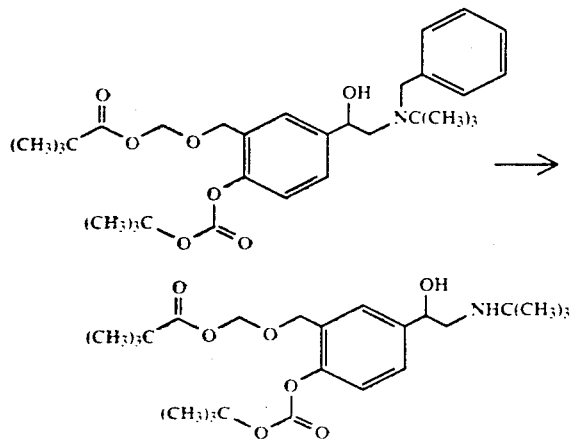

The starting material (0.849 g) prepared as described in Preparative Example 11, was dissolved in IPA, to which was added 10% Pd-C (85 mg) and acetic acid (0.11 mL). The mixture was stirred in a hydrogen atmosphere and the reaction was followed by TLC. When the reaction was complete (ca. 4 hr.) the catalyst was filtered off and solvents were removed under vacuum. The residue was dried under high vacuum, triturated with hexane, then dried under high vacuum for 2½ days to yield the acetate salt of the desired product as a hygroscopic glassy solid, 0.35 g.

Analysis: For $C_{24}H_{30}NO^-·CH_3CO_2H$. Found: C, 60.43; H, 8.24; N, 2.71. Theory: C, 60.80; H, 8.44; N, 2.72.

FAB-MS; m/e 454 (M+1).

EXAMPLE 4

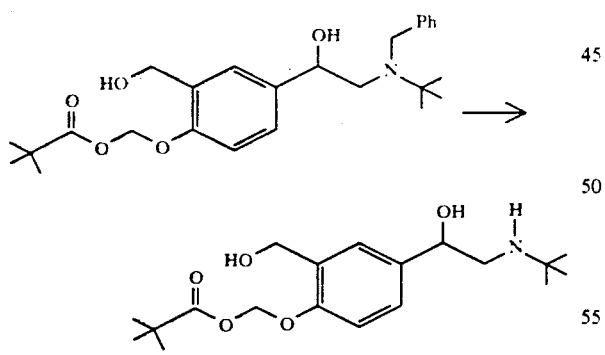

The product from Prep. Example 4 (0.85 g) was dissolved in IPA (8 mL). To this solution was added 20% HCl in methanol (0.53 mL), and the solvent was removed by evaporation. The residue was dissolved in IPA (20 mL) and 10% Pd-C (86 mg) was added. The mixture was stirred and hydrogenolyzed at 1 atmos. until the reaction was completed (TLC).

The reaction mixture was filtered and evaporated to dryness under vacuum. The residue was purified by chromatography on a silica gel column eluting with CH₂Cl₂/12% methanol. Fractions containing the desired product were combined and evaporated to dryness over night. The yield of desired product as a hygroscopic white solid, was 0.06 g.

Analysis: For $C_{19}H_{31}NO_5·HCl·H_2O$. Found: C, 55.40; H, 7.61; N 3.26. Theory: C, 55.94; H, 8.40; N, 3.43.

FAB-MS; m/e 354 (M+1).

EXAMPLE 5

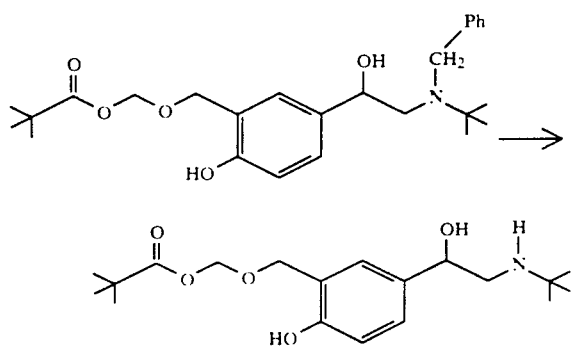

The product from Preparative Example 7 (0.65 g) was dissolved in IPA (10 mL), and 20% HCl in methanol (0.3 mL) was added. After stirring for 5 min. the solvent was removed by evaporation under vacuum. The residue was redissolved in CH₂Cl₂/IPA (13 mL of 1:1), and 5% Pd-C (65 mg) was added. The mixture was stirred in an atmosphere of H₂ for 2 h. The catalyst was removed by filtration through a Celite pad which was then rinsed with CH₂Cl₂/IPA (20 mL of 1:1). The solvents were removed by evaporation under vacuum. The crude product was purified by column chromatography on silica gel eluting with 10% methanol/CH₂Cl₂. Fractions containing the product, as shown by TLC, were combined and evaporated to yield a product which was further purified by trituration with CH₂Cl₂/ether to yield the desired product, as the hydrochloride salt, as a white solid, 0.34 g, mp 181°–184° C.

Analysis: For $C_{19}H_{31}NO_5·HCl$. Found: C, 58.52; H, 8.35; N, 3.48; Cl, 9.04. Theory: C, 58.67; H, 8.27; N, 3.59; Cl, 9.09.

FAB-MS; m/e 354 (M+1).

EXAMPLE 6

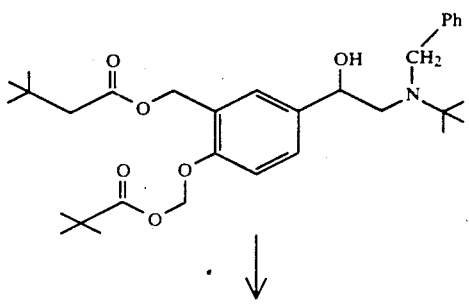

-continued

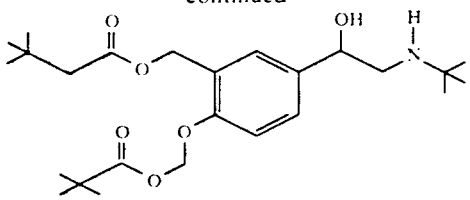

The product from Preparative Example 6 (0.7 g) was dissolved in IPA (14 mL) and 20% HCl/methanol (0.3 mL) was added. The mixture was stirred for 5 minutes. The solvents were removed under vacuum and the residue was dissolved in IPA (14 mL). To this solution was added 10% Pd-C (17 mg) and the mixture was hydrogenolyzed at 1 atmosphere. The reaction was followed by TLC and was complete after about 2 hours. The mixture was filtered, and solvents were evaporated under vacuum. The residue was purified by flash chromatography on silica gel eluting with CH$_2$Cl$_2$: methanol (9:1). Fractions containing the desired product were combined and evaporated to a white solid m.p. 40°–41° C. (0.41 g).

Analysis: For C$_{25}$H$_{41}$NO$_6$. HCl. Found: C. 61.16; H. 8.68; N. 2.75. Theory: C. 61.52; H. 8.67; N. 2.87.

FAB-MS: m/e 452 (M−1).

EXAMPLE 7

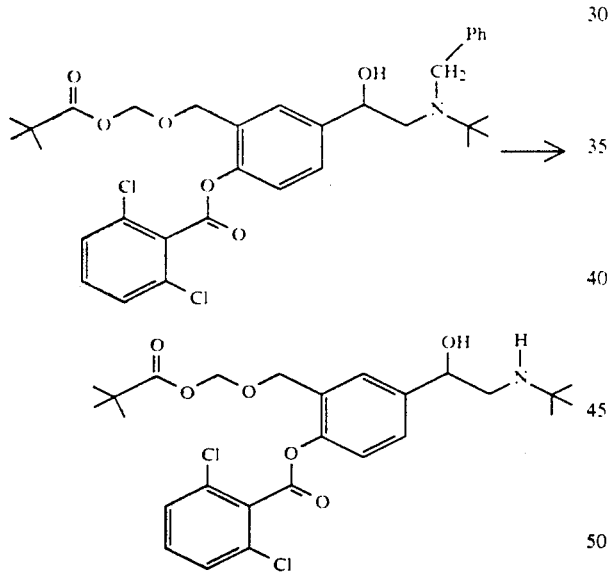

The product from Preparative Example 8 (0.933 g) was dissolved in CH$_2$Cl$_2$ and to the solution was added 20% HCl in methanol (0.33 mL). The mixture was stirred for 5 min then it was evaporated under vacuum to yield a white, fluffy solid.

This salt was dissolved in CH$_2$Cl$_2$/IPA (10 mL of 1:1) contained in a hydrogenation vessel. To the solution was added 10% Pd-C (98.5 mg) under an atmosphere of N$_2$. The suspension was stirred in an atmosphere of H$_2$ for 2 h. It was filtered, and evaporated under vacuum to yield an amber oil. This crude product was purified by short-path column chromatography over silica gel, eluting with 5% methanol/CH$_2$Cl$_2$. After locating the product by TLC the relevant fractions were evaporated to yield the desired product, as its HCl salt, 0.35 g, mp 75°–77° C.

Analysis: For C$_{26}$H$_{33}$NO$_6$Cl$_2$.HCl. Found: C. 55.48; H. 5.99; N. 2.40. Theory: C. 55.42; H. 6.09; N. 2.49.

By one of essentially the same procedures as described in Examples 6 and 7, using minor modifications well known to one skilled in the art, were prepared:

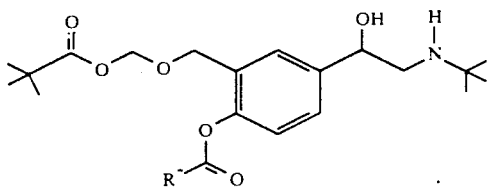

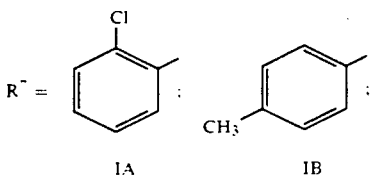

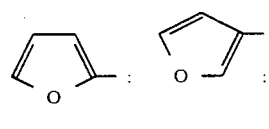

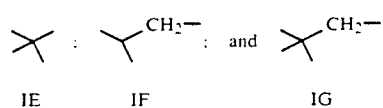

Compound (IA); mp 47°–49° C.
Analysis: For C$_{26}$H$_{34}$NO$_6$Cl.HCl. Found: C. 59.73; H. 6.76; N. 2.65. Theory: C. 59.09; H. 6.68; N. 2.65.
FAB-MS; m/e 492/494. (M+1).

Compound (IB); mp 53°–55° C.
Analysis: For C$_{27}$H$_{37}$NO$_6$. HCl. Found: C. 63.87; H, 7.51; N, 2.62; Cl, 6.81. Theory: C, 63.83; H, 7.53; N, 2.75; Cl, 6.97.
FAB-MS; m/e 472, (M+1).

Compound (IC); mp 54°–57° C.
Analysis: For C$_{24}$H$_{33}$NO$_7$.HCl.H$_2$O. Found: C, 57.85; H, 7.09; N, 2.70; Cl, 6.66. Theory: C, 57.42; H, 7.22; N, 2.78; Cl, 7.06.
FAB-MS; m/e 488 (M+1).

Compound (ID)
Analysis: For C$_{24}$H$_{33}$NO$_7$.HCl. Found: C, 59.22; H, 7.02; N, 2.76; Cl, 6.76. Theory: C, 59.56; H, 7.08; N, 2.89; Cl, 7.33.
FAB-MS; m/e 448 (M+1).

Compound (IE)
Analysis: For C$_{24}$H$_{39}$NO$_6$.HCl. Found: C, 60.55; H, 8.70; N, 2.85; Cl, 7.10. Theory: C, 60.80; H, 8.50; N, 2.95; Cl, 7.47.
FAB-MS; m/e 438 (M+1).

Compound (IF) mp 168°–171° C.
Analysis: For C$_{24}$H$_{39}$NO$_6$.HCl. Found: C, 60.45; H, 8.30; N, 2.88. Theory: C, 60.80; H, 8.50; N, 2.95.
FAB-MS; m/e 438 (M+1).

Compound (IG); C$_{25}$H$_{41}$NO$_6$
FAB-MS; m/e 452 (M+1).

EXAMPLE 8

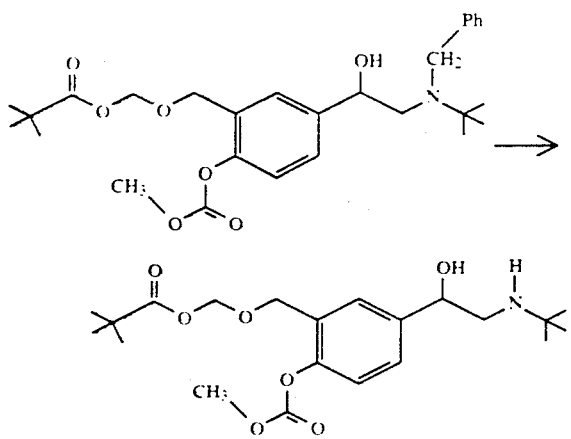

The product from Preparative Example 9 (0.24 g) was dissolved in IPA (5 mL), and 20% HCl in methanol (0.1 mL) was added. After 5 min. of stirring at room temperature the solvents were evaporated off under vacuum. The residue was dissolved in IPA (7 mL), 10% Pd-C (24 mg) was added, and the mixture was hydrogenolyzed at room temperature and at 1 atmos. for about 2 h. The catalyst was removed by filtration through a Celite pad which was rinsed with $CH_2Cl_2$ (50 mL). The combined organic solutions were evaporated under vacuum, and the resulting solid was triturated with ether to yield the desired product as a white, hygroscopic powder.

Analysis: For $C_{21}H_{33}NO_7 \cdot HCl$. Found: C, 56.31; H, 7.76; N, 3.01. Theory: C, 56.31; H, 7.65; N, 3.13.

FAB-MS: m/e 412 (M+1).

EXAMPLE 9

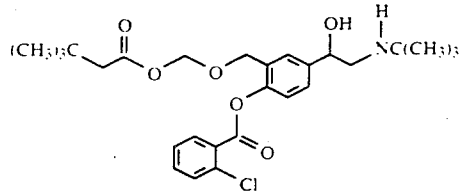

The product from Preparative Example 3, (2.39 g) was dissolved/suspended in $CH_2Cl_2$ (238 mL). A slight excess of 20% HCl in methanol (0.88 mL) was added. The mixture was stirred for 10 min. and was then evaporated to a white solid. This solid was redissolved in ethanol (239 mL). To this solution was added 10% Pd-C (1.195 g) while the flask was flushed with $N_2$. The mixture was stirred and hydrogenolyzed under 1 atmos. of $H_2$. The progress of the reaction was followed at ca. 15 min. intervals by reverse-phase HPLC. The reaction was terminated when dechlorination of the aromatic halogen began to be seen (ca. 2% conversion to dechlorinated product; trace of starting material left).

The catalyst was filtered off, and the reaction mixture was evaporated to dryness under vacuum. The crude product was dissolved in a mixture of $CH_2Cl_2$ (90): IPA (10) and was purified on a short-path silica gel column made up in the same solvent. Fractions eluting from the column were monitored by RP-HPLC using an ODS-3 analytical column, eluting with methanol (80):water (20):$H_3PO_4$(1):sodium dodecyl sulfate (0.0025M) and detecting by UV absorption at 230 nM. Fractions containing product were combined and concentrated to a colorless sirup. This thick oil was dissolved in deionized water and was lyophilized to a white powder.

Analysis: For $C_{27}H_{36}NO_6Cl \cdot HCl$. Found: C, 59.20; H, 7.20; N, 2.58. Theory: C, 59.77; H, 6.87; N, 2.58.

FAB-MS: m/e 506/508 (M+1 for $^{35}Cl$ and $^{37}Cl$ respectively).

By an analogous procedure, using minor modifications well known to one skilled in the art, the compound shown below was prepared. For instance, the salt used in the debenzylation was derived from trifluoroacetic acid instead of HCl.

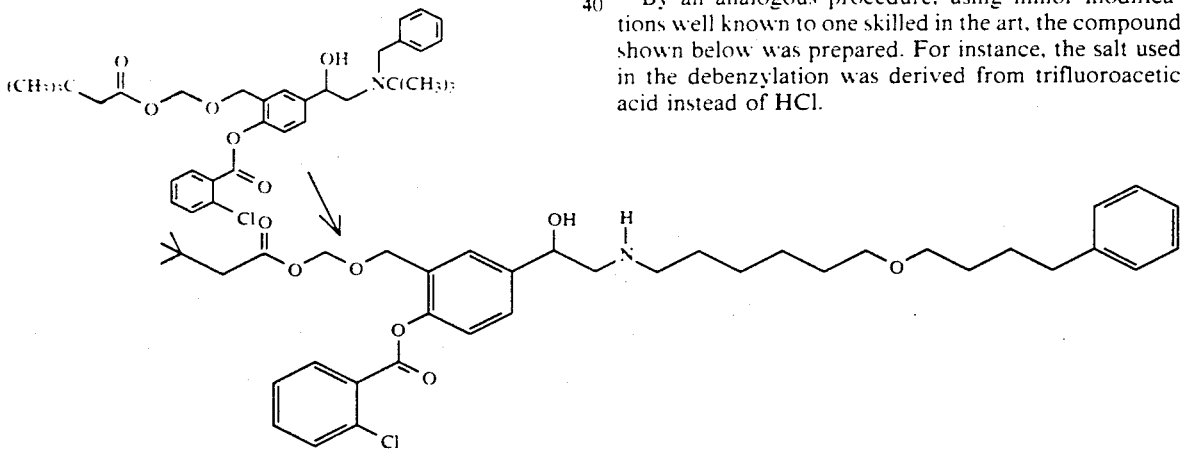

$C_{39}H_{53}NO_7Cl$; FAB-MS MW (of M+1 ion containing the $^{35}Cl$ isotope) by peak matching = 682.3534 (calculated value, 682.3511).

EXAMPLE 10—AEROSOL FORMULATION

A suspension aerosol is made according to the following directions. Disperse a suitable surfactant, such as oleic acid, Span 85 (sorbitan trioleate), oleyl alcohol, sorbitan monooleate, or soy lecithin (10 to 400 mg/aerosol can) with agitation in an aerosol holding maintained at 30° F. (−2° C.). Add the following compound of formula I

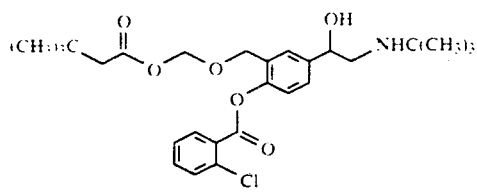

(50 to 400) mg/aerosol can) in micronized form, and continue agitation. (Other compounds of formula I may also be used in this example.) Cover the tank and overlay the concentrated suspension/solution with nitrogen. Run the concentrate into the aerosol cans, fit a valve on each can and crimp on to the can. Finally, charge Freon 12 (dichlorodifluoromethane: 12 to 20 g/aerosol can) through the valve. Propellants other than Freon 12; such as Freon 114 (1,2-dichloro-1,1,2,2-tetrafluoroethane) may be used. Non-Freon propellants may also be used.

PREPARATIVE EXAMPLE 1

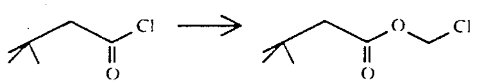

A mixture of t-butylacetylchloride (30 g) and paraformaldehyde (6.75 g) was heated under $N_2$ at 130° C. The original suspension eventually became a clear solution. The reaction was followed by TLC (Thin Layer Chromatography) using $CH_2Cl_2$, visualized with iodine. Reaction was complete after about 72 hr. The crude product was purified by flash chromatography on silica gel eluting with $CH_2Cl_2$. Evaporation of the fractions containing product yielded 23.3 g of a clear liquid.

-continued

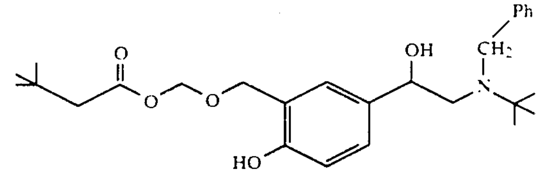

A mixture of the product from Prep. Example 1 (5 g), potassium iodide (11.6 g) and acetone (250 mL) was stirred under $N_2$ at room temperature for 2½ days. The mixture was filtered and the red solution retained.

To a solution of $\alpha^1$-[[(1,1-dimethylethyl)phenylmethyl amino]methyl]-4-hydroxy-1,3-benzenedimethanol (9.0 g) in acetone (50 mL), under nitrogen, was added powdered, anhydrous potassium carbonate (2.25 g) and the mixture was stirred for 1 hr. at room temperature. The red solution (from above) was added to this suspension over a period of less than 1 minute. Stirring was continued at room temperature. The reaction was followed by TLC (silica gel/hexane:ethylacetate 1:1) until no further changes occured.

The solids were filtered off, and solvents were removed under vacuum at or below room temperature. The residue was extracted with hexane:ethyl acetate 1:1 containing some $CH_2Cl_2$.

The solution was chromatagraphed on silica gel, eluting with hexane:ethyl acetate 1:1 to yield 2.5 g of a viscous oil which was stored under $N_2$ in the freezer. The $^1$H-NMR was consistent with the assigned structure.

$C_{27}H_{39}NO_5$; MW457; FAB-MS m/e458(M+1)

In the above example, and throughout the specification, Ph denotes phenyl.

By a process essentially the same as that described in Preparative Example 2 was prepared the following compound:

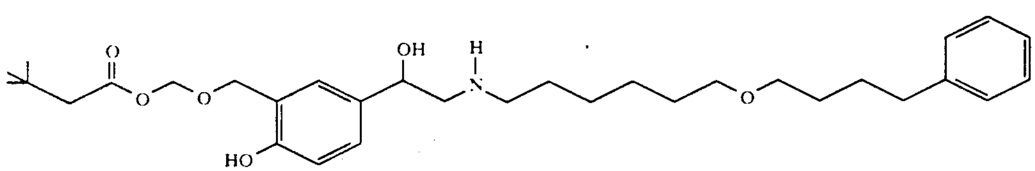

The product was stored under $N_2$ in the refrigerator. It was characterized by its $^1$H-NMR spectrum which showed the expected two methylene singlets (2×2H) and a singlet for the t-butyl group (9H).

PREPARATIVE EXAMPLE 2

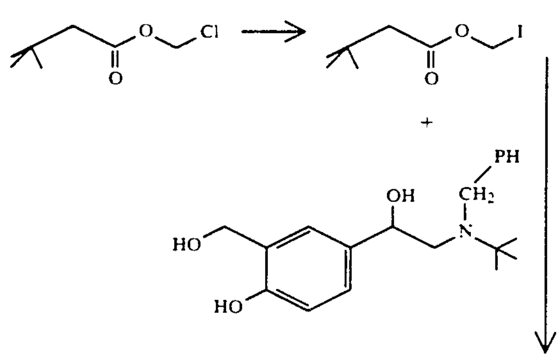

$C_{39}H_{55}NO_6$; FAB-MS, m/e634(M+1).

PREPARATIVE EXAMPLE 3

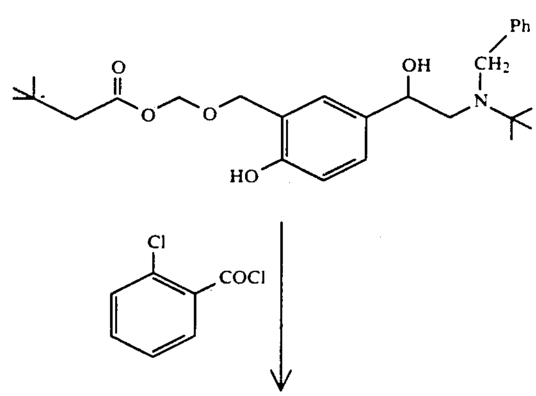

-continued

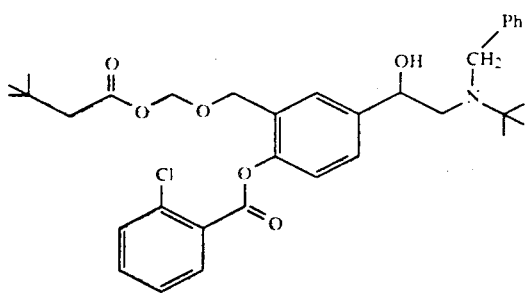

The product from Preparative Example 2 (8.5 g) was dissolved in dry CH₂Cl₂ (255 mL) under N₂ with stirring. The solution was cooled to about −78° C. Triethylamine (2.24 g) was added dropwise over a period of about 30 min. After about 15 min of additional stirring, distilled o-chlorobenzoyl chloride (3.98 g) in dry CH₂Cl₂ (85 mL) was added to this solution dropwise over a period of about 30 min. The reaction was then kept in a −70° C. freezer for 2 and one half days.

The solvent was removed under high vacuum, the residue was added to a hexane/ethyl acetate mixture (75 mL of 1:1). A white solid (4.85 g) precipitated out and was filtered off (see later). The solution was evaporated to dryness again and was redissolved in CH₂Cl₂:CH₃OH (95:5). It was purified first by flash chromatography on silica gel eluting with CH₂Cl₂:CH₃OH (95:5). A second column was run with CH₂Cl₂:acetone (95:5) to elute a non-polar by-product, followed by CH₂Cl₂:CH₃OH (95:5) and CH₂Cl₂:CH₃OH (90:10) to elute the desired product. Evaporation of fractions containing the product, as shown by TLC, yielded the desired product 2.33 g.

PREPARATIVE EXAMPLE 4

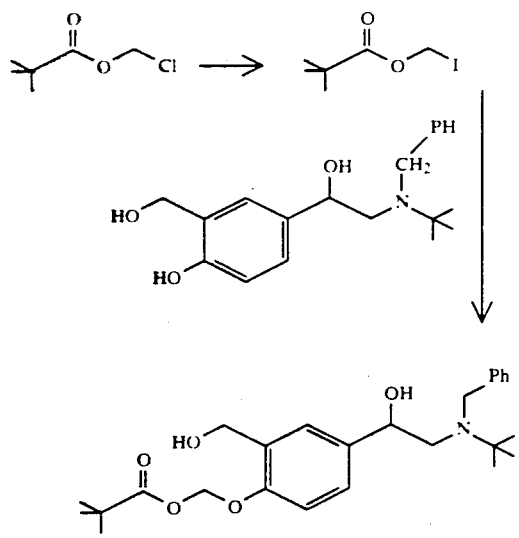

Chloromethyl pivalate (1.94 mL) was dissolved in dry acetone (120 mL). Potassium iodide (dry; 3.68 g) was added and the reaction was stirred at room temperature for 4 days. The solids were filtered off to produce a clear red solution. To this mixture, which had turned a dark red color, was added anhydrous, powdered potassium carbonate (2.55 g), followed by α¹-[[1,1-dimethylethyl)phenylmethylamino]methyl]-4-hydroxy-1,3-benzenedimethanol (5.13 g). The reaction was followed by TLC until no further changes occurred. The solution had changed color to a pale yellow.

The reaction mixture was filtered and solvent was removed by evaporation under vacuum, and a residue was dissolved in CH₂Cl₂:IPA (96:4; 15 mL). The solution was separated on a silica gel column, eluting with increasing concentrations of IPA in CH₂Cl₂. Fractions containing the desired product were evaporated to yield 1.76 g of the desired product as an oil. Characterization was by ¹H-NMR and Fast Atom Bombardment Mass Spectrometry (FAB-MS) which showed m/e 444(M+1) as expected for this product.

PREPARATIVE EXAMPLE 5

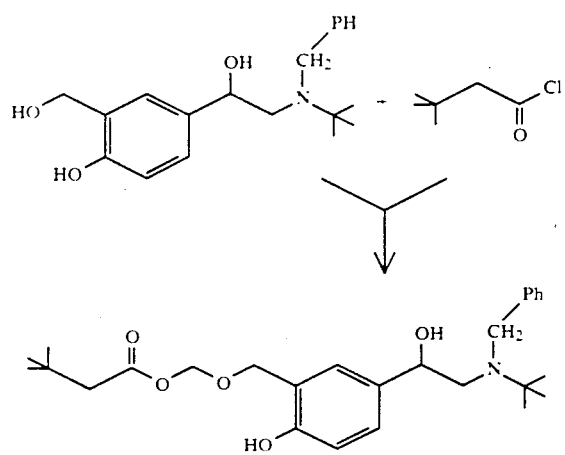

α¹-[[(1,1-Dimethylethyl)-phenylmethyl amino]methyl]-4-hydroxy-1,3-benzenedimethanol (20 g) was dissolved in CH₂Cl₂ (200 mL) and stirred under N₂. Triethylamine (16.9 mL) was added to the solution. The reaction flask was cooled in an IPA/Dry Ice bath to −78° C. After 0.25 h, t-butylacetyl chloride (9.3 mL) was added dropwise. The mixture was stirred for 2 h and the reaction was followed by TLC. It was allowed to warm to room temperature (RT) and stirred overnight. Triethylamine (4.2 mL, 0.5 equivs.) was added and stirring was continued at RT until TLC showed that the reaction was complete. The solvents were removed under vacuum, and the product was purified by column chromatography to yield 13.83 g (53%) of the desired product as an oil. It was characterized by FAB-MS; m/e 428 (M+1).

PREPARATIVE EXAMPLE 6

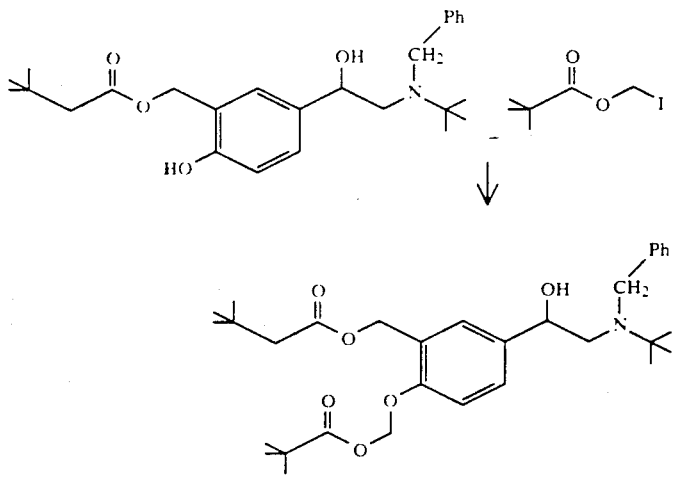

The product from Prep. Example 5 (1.5 g) was dissolved in acetone (dry: 22.5 mL). To this solution was added anhdrous, powdered potassium carbonate (0.58 g) and then very slowly iodomethyl pivalate (23.1 mL containing 3.85 mmol, 10% excess) in a N₂ atmosphere.

When the reaction was complete (as determined by TLC) the solids were filtered off and the solvent was removed under reduced pressure. The product was purified by chromatography on the silica gel column eluting with CH₂Cl₂:ethyl acetate (9:1). Fractions containing the product were combined and evaporated to yield (0.72 g) the desired product as a white foam. It was characterized by ¹H-NMR and FAB-MS (m/e 542; M−1).

PREPARATION EXAMPLE 7

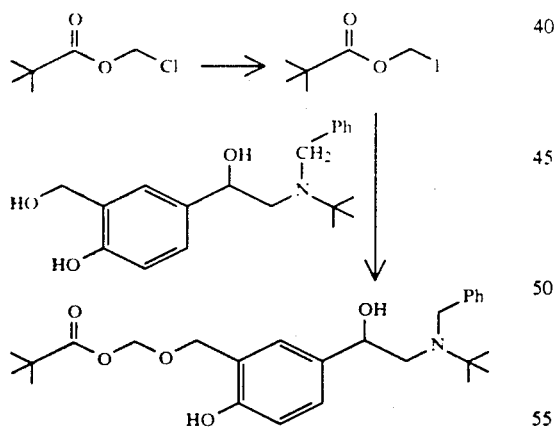

Chloromethyl pivalate (6 mL) was dissolved in dry acetone (500 mL) in an atmosphere of N₂. To the mixture was added dry potassium iodide (15.33 g), and the mixture was stirred at room temperature for two days. After this time the mixture was filtered to yield a clear solution of iodomethyl pivalate.

In dry acetone (100 mL), under an atmosphere of N₂, was dissolved α¹-[[(1,1-dimethylethyl)-phenylmethyl amino]methyl]-4-hydroxy-1,3-benzenedimethanol (10 g), and to the solution was added anhydrous potassium carbonate (5 g). The mixture was stirred for 10 min, then the solution of iodomethyl pivalate (456 mL) was added rapidly at room temperature. The resulting mixture was stirred for one day at room temperature.

The solids were filtered off and rinsed with fresh acetone. The combined acetone solutions were evaporated under vacuum to a viscous oil which was redissolved in CH₂Cl₂ (200 mL). This solution was treated with H₂O (300 mL) and the pH of the aqueous phase was adjusted to 7.0 with acetic acid. After separation, the aqueous phase was extracted with CH₂Cl₂(3×200 mL). The combined organic extracts were washed with H₂O, dried (MgSO₄) and evaporated to yield ca. 15 g of crude product mixture.

Purification was achieved by column chromatography on silica gel, eluting with 4% IPA in CH₂Cl₂ to yield the desired product (3.6 g) as a clear oil. Characterization was by ¹H-NMR and FAB-MS (m/e 444; M+1).

PREPARATIVE EXAMPLE 8

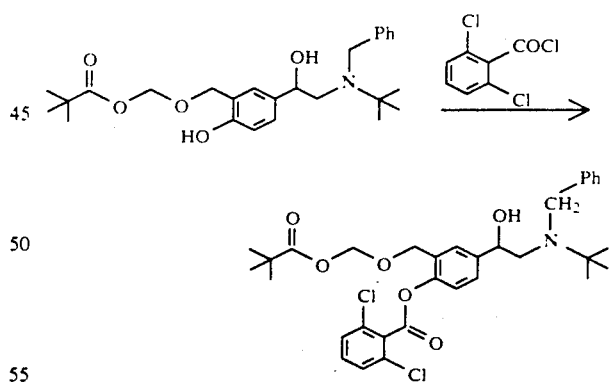

The product was Preparative Example 7 (0.69 g) was dissolved, with stirring, in CH₂Cl₂ (8 mL) in an atmosphere of N₂, and the solution was cooled to below −70° C. in a Dry-Ice/acetone bath. To the solution was added triethylamine (0.238 mL) and stirring was continued for 15 min. After this time 2,6-dichlorobenzoyl chloride (0.231 mL) was added dropwise by syringe to the cold solution. The reaction was allowed to warm gradually to room temperature and its progress was followed by TLC. After about 4 days an additional quantity of the acid chloride (0.055 mL) was added, and stirring was continued for one more day.

The reaction mixture was evaporated to dryness under vacuum to yield a crude mixture which was redissolved in 5% ethyl acetate/CH₂Cl₂ and purified by short-path column chromatography on silica gel, eluting with the same solvent. The desired product was obtained by evaporation of those fractions show (by TLC) to contain it. It was obtained as a white foam, 0.93 g, and was characterized by ¹H-NMR.

By essentially the same procedure, with slight modifications well known to one skilled in the art, the following intermediates were prepared:

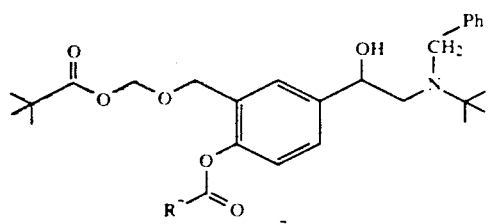

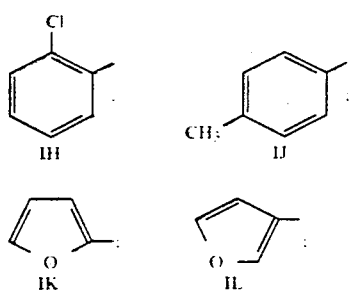

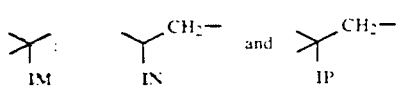

PREPARATIVE EXAMPLE 9

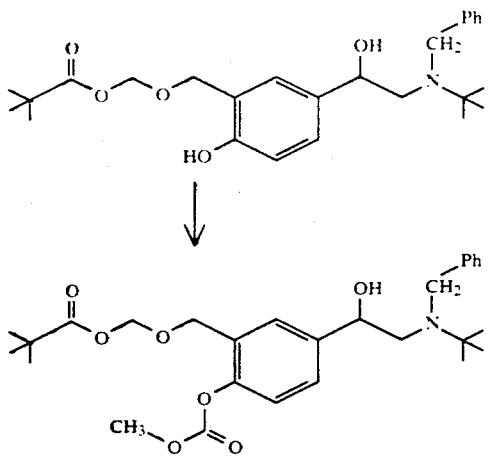

To a solution of the product from Preparative Example 7 (0.6 g) in CH₂Cl₂ (6 mL) was added triethylamine (0.207 mL). The reaction flask was flushed with Ar then cooled to below −70° C. and kept in an atmosphere of N₂. To the cooled solution was added methyl chloroformate (0.11 mL) and the flask was stirred at below −70° C. for 4 h. After warming to room temperature the solvent was evaporated under vacuum. The crude product was separated by flash column chromatography on silica gel, eluting with 10% ethyl acetate/CH₂Cl₂. The desired product was isolated from the relevant fractions, as shown by TLC, by evaporation and used without further purification. (see Example 8). It was obtained as a foam, 0.24 g, and was characterized by its ¹H-NMR spectrum.

PREPARATIVE EXAMPLE 10

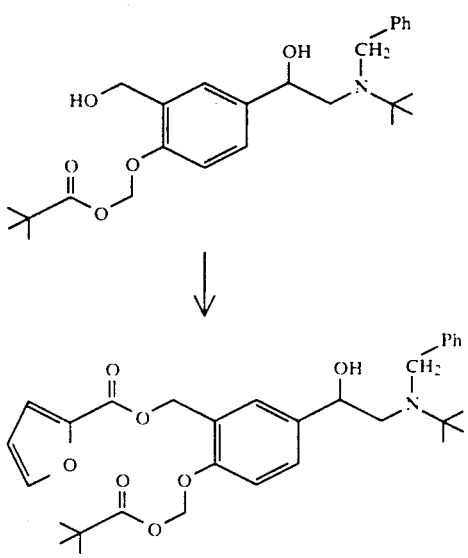

The product from Preparative Example 4 (1 g) was dissolved in CH₂Cl₂, under an atmosphere of N₂, and was chilled in an IPA/Dry-Ice bath to below −70° C. Triethylamine (0.377 mL) was added by syringe, followed by α-furoyl chloride (0.246 mL). The reaction was kept below −70° C. overnight then it was followed by TLC. After about 5 days the reaction was essentially complete. The solvents were evaporated off under vacuum, and the crude product was purified by short-path column chromatography, eluting the CH₂Cl₂. The desired product was isolated from the relevant fractions, as shown by TLC, by evaporation under vacuum to yield a clear oil, 0.28 g. Characterization was by ¹H-NMR. The product was used in the next step without further purification.

By essentially the same procedure, using minor modifications well known to one skilled in the art, was prepared:

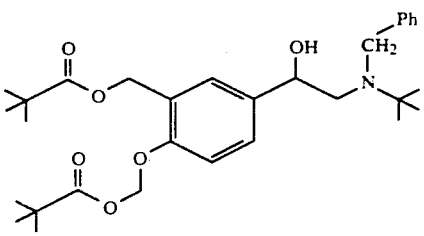

PREPARATIVE EXAMPLE 11

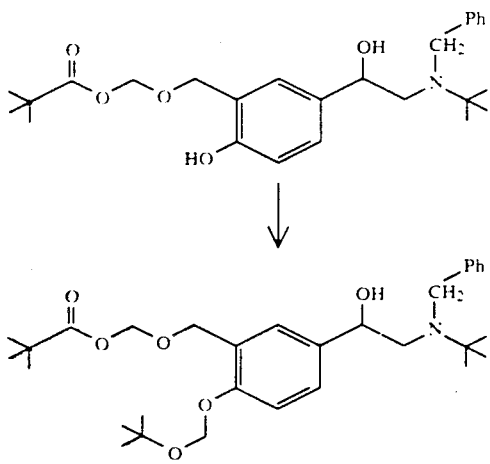

The product from Preparative Example 7 (2.0 g) was dissolved in dry pyridine, under an atmosphere of N$_2$, and was treated with di-tert-butyl dicarbonate (t-BOC anhydride; 1.32 g) at room temperature. The mixture was stirred for 3 days. The reaction mixture was evaporated to dryness under vacuum and the crude product was dissolved in 20% ethyl acetate in hexane. This solution was separated by column chromatography on silica gel, eluting with the same solvent as was used for dissolution of the sample. The product so obtained showed the correct MW by FAB-MS (m/e 544.8; M – 1) but appeared to contain a trace of impurity. Therefore, it was subjected to a further purification by flash column chromatography on silica gel, eluting with 40% ethyl acetate in hexane. Elution was followed by TLC, and the relevant fractions were combined and evaporated to yield the desired product, 0.83 g, as a yellow oil, which was characterized by its $^1$H-NMR spectrum.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed:

1. A compound of the formula I

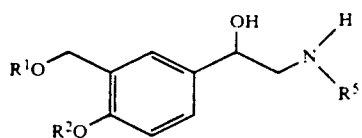

wherein
R$^5$ represents C$_1$ to C$_6$-alkyl or the group —(CH$_2$)$_n$—Z—(CH$_2$)$_m$—Ar;
Z represents O, S or —CH$_2$—;
n represents an integer of 1 to 8;
m represents zero or an integer of 1 to 8;
one of R$^1$ and R$^2$ represents the group

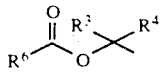

and the other represents hydrogen or R$^7$CO—;
R$^7$ is C$_1$ to C$_{10}$ alkyl, C$_3$ to C$_8$ cycloalkyl, aryl, heteroaryl having at least one O, S, and/or N interrupting a carbocyclic ring structure with the aromatic heterocyclic group having from 2 to 14 carbon atoms, —N(R$^9$R$^{10}$), or R$^{11}$O—; R$^3$, R$^4$, R$^9$, and R$^{10}$ are each independently selected form hydrogen, C$_1$ to C$_6$ alkyl and Ar$^1$; R$^6$ and R$^{11}$ are each independently C$_1$-C$_8$ alkyl; Ar and Ar$^1$ are each independently selected from the group consisting of phenyl or phenyl substituted by one or two substituents selected from the group consisting of R$^{12}$, R$^{13}$O—, R$^{14}$S(O)$_x$—, R$^{15}$CO—, (R$^{16}$R$^{17}$)NCO—, F, Cl, Br, I, NO$_2$, CF$_3$, CN, or phenyl; R$^{12}$, R$^{13}$, R$^{14}$, R$^{15}$, R$^{16}$, and R$^{17}$ each independently represents an alkyl group having 1 to 6 carbon atoms; x is 0, 1, 2;
or a pharmaceutically acceptable acid addition salt thereof.

2. A compound according to claim 1, in the form of a pharmaceutically acceptable acid addition salt.

3. A compound according to claim 2, wherein R$^1$ represents

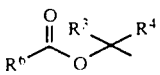

and R$^2$ represents

R$^7$—CO— wherein R$^3$, R$^4$, R$^6$ and R$^7$ are as defined in claim 1.

4. A compound according to claim 2, wherein R$^1$ represents

R$^7$—CO— and R$^2$ represents

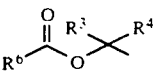

wherein R$^3$, R$^4$, R$^6$ and R$^7$ are as defined in claim 1.

5. A compound according to claim 3 or 4, wherein R$^5$ represents tert-C$_4$H$_9$, iso-C$_3$H$_7$ or —(CH$_2$)$_n$—Z—(CH$_2$)$_m$—Ar wherein n and m independently are integers of 2 to 6, Z represents O and Ar is phenyl.

6. A compound according to claim 5, wherein R$^3$ and R$^4$ both represent H.

7. A compound according to claim 6, wherein R$^6$ represents C$_3$ to C$_6$ alkyl.

8. A compound according to claim 7, wherein R$^7$ represents C$_1$ to C$_6$ alkyl, phenyl, substituted phenyl, or unsubstituted heteroaryl.

9. A compound according to claim 7, wherein R$^7$ represents C$_1$ to C$_6$ alkyl, phenyl or substituted phenyl.

10. A compound in accordance with claim 1, having the structural configuration

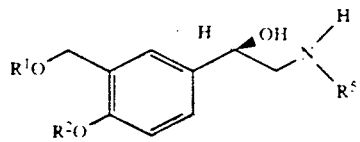
wherein $R^1$, $R^2$ and $R^5$ are as described in claim 1.
11. A compound according to claim 3 or 4, having the structural formula
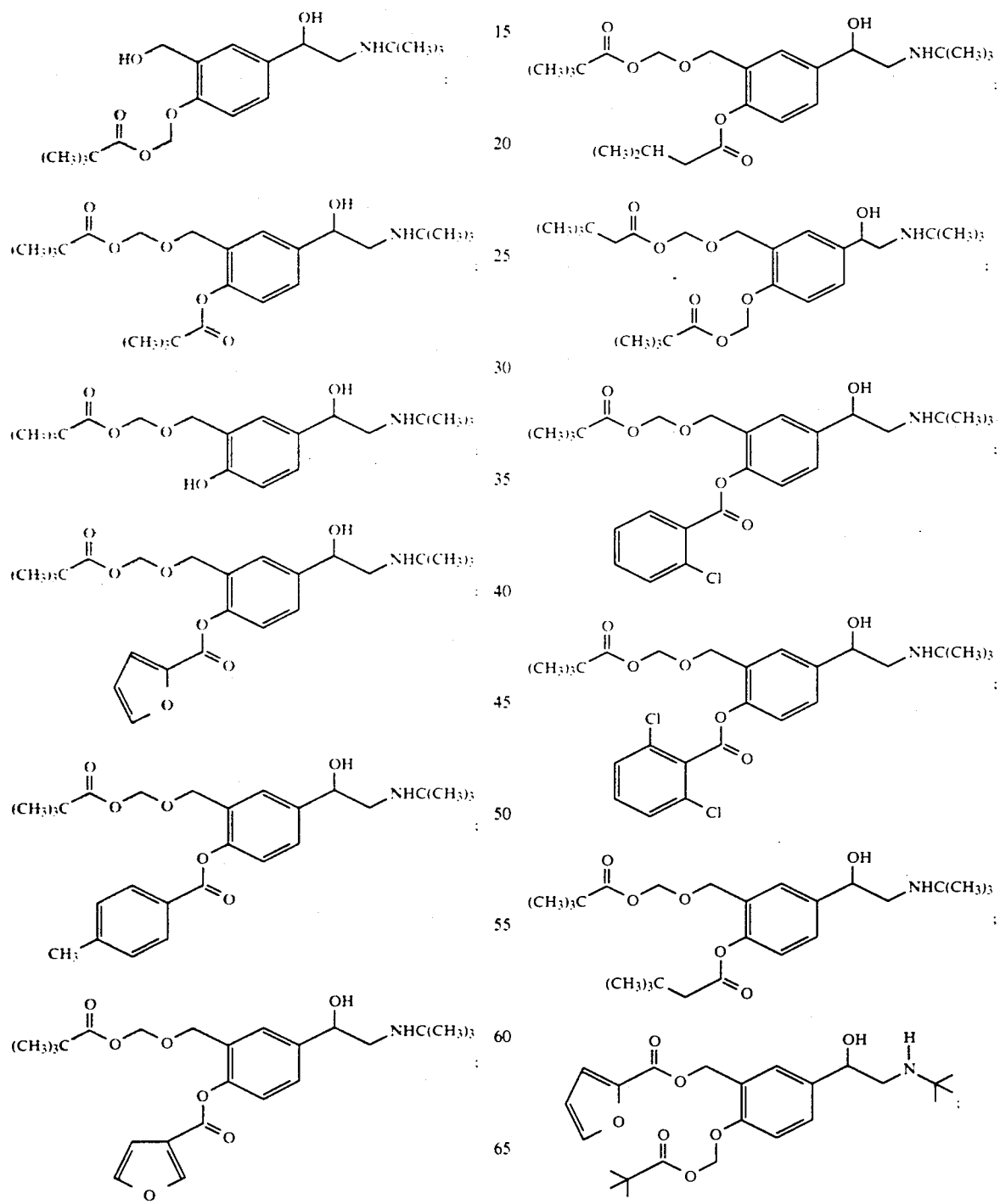

-continued

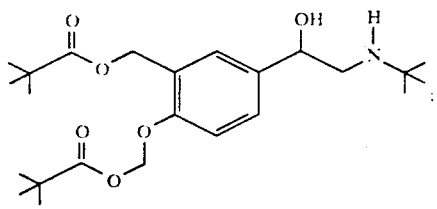

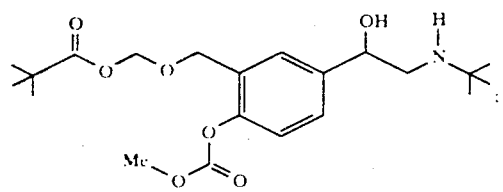

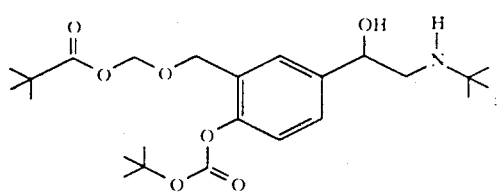

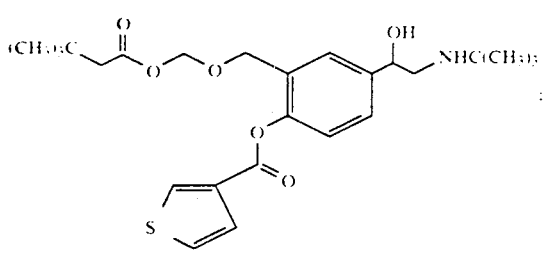

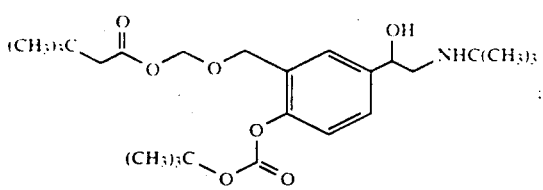

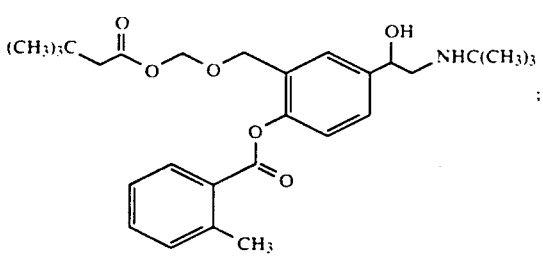

-continued

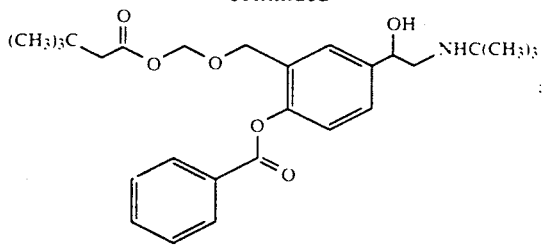

or

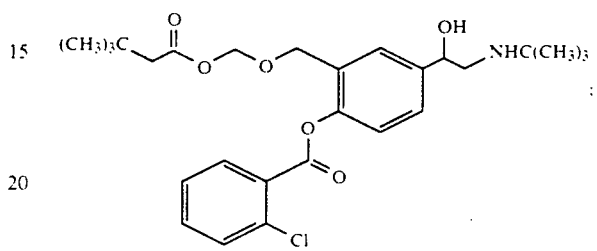

or a pharmaceutically acceptable acid addition salt thereof.

12. A compound according to claim 2 having the structural formula

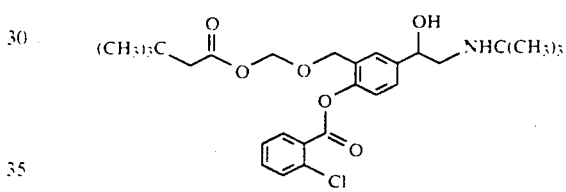

or a pharmaceutically acceptable acid addition salt thereof.

13. A compound in accordance with claim 12 having the formula

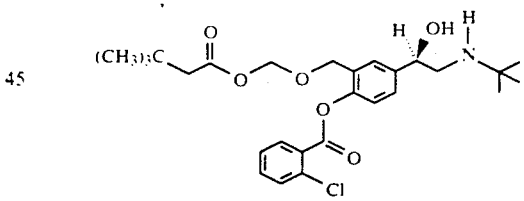

or a pharmaceutically acceptable addition salt thereof.

14. A pharmaceutical composition comprising as an active ingredient a compound as defined in claim 1 in combination with a pharmaceutically acceptable carrier.

15. A method of treating obstructive pulmonary disease comprising administering an effective amount of a compound as defined in claim 1.

16. A method according to claim 15, wherein the compound of formula I is administered by inhalation.

17. A method of treating asthma and asthmatic bronchitis comprising administering an effective amount of a compound as defined in claim 1.

18. A method according to claim 17 wherein the compound of formula I is administered by inhalation.

* * * * *